US012642923B2

(12) United States Patent
Stuart et al.

(10) Patent No.: US 12,642,923 B2
(45) Date of Patent: Jun. 2, 2026

(54) DRIVE MECHANISM

(71) Applicant: Merxin Ltd, King's Lynn (GB)

(72) Inventors: Adam Stuart, King's Lynn (GB);
Stephen Howgill, Leicester (GB)

( * ) Notice: Subject to any disclaimer, the term of this patent is extended or adjusted under 35 U.S.C. 154(b) by 777 days.

(21) Appl. No.: 18/062,753

(22) Filed: Dec. 7, 2022

(65) Prior Publication Data

US 2024/0189525 A1    Jun. 13, 2024

(51) Int. Cl.
*A61M 15/00* (2006.01)

(52) U.S. Cl.
CPC .... *A61M 15/0065* (2013.01); *A61M 15/0026* (2014.02); *A61M 15/0051* (2014.02)

(58) Field of Classification Search
CPC ................................................ A61M 15/0026
See application file for complete search history.

(56) References Cited

U.S. PATENT DOCUMENTS

2021/0268214 A1* 9/2021 Clarke .............. A61M 15/0003

FOREIGN PATENT DOCUMENTS

| EP | 3622990 A1 | 3/2020 |
| WO | 2007/012871 A1 | 2/2007 |
| WO | 2010135253 A2 | 11/2010 |
| WO | 2021195353 A1 | 9/2021 |

OTHER PUBLICATIONS

International Search Report and Written Opinion issued for International Patent Application PCT/IB2023/062367, on Mar. 1, 2024, 10 Pages.
Combined Search and Examination Report under Sections 17 and 18(3) issued for United Kingdom Patent Application GB2218391.7, on May 18, 2023, 06 Pages.

* cited by examiner

*Primary Examiner* — Bradley H Philips
(74) *Attorney, Agent, or Firm* — RC Trademark Company

(57) ABSTRACT

In general terms the present invention proposes a medicament dispenser 100 for use with at least one medicament carrier carrying multiple distinct medicament dose portions. The medicament dispenser 100 comprises: (a) a dispensing mechanism actuable for dispensing the dose portions carried by the at least one medicament carrier; (b) a mouthpiece 106; and (c) a cover for the mouthpiece, the cover being movably mounted to the dispenser 100 for sequential movement from a closed position in which the mouthpiece 106 is at least partially covered, to an open position in which the mouthpiece 106 is uncovered, via a first position, and optionally via a second position between the first position and the closed position that includes the closed position.

15 Claims, 14 Drawing Sheets

DRIVE MECHANISM

TECHNICAL FIELD

This invention relates to medicament dispensers for dispensing medicament. In particular, though not exclusively, this invention relates to a medicament dispenser for use with at least one medicament carrier carrying multiple distinct medicament dose portions.

BACKGROUND

The use of a dry powder inhaler (DPI) devices in the administration of medicaments, for example in bronchodilation therapy is well known. Such devices generally comprise a housing within which a supply of medicament is located. Known inhalation devices include those in which supply of medicament is in the form of a blister strip comprising a plurality of blister pockets each defining discrete dose portions of a dry powder medicament. Such devices usually contain a mechanism for accessing these doses, usually comprising either piercing means or means to peel a lid sheet away from a base sheet. The powdered medicament can then be accessed and inhaled by the patent through a mouthpiece.

With such devices, access to each dose is typically enabled on a serial basis by advancing the strip within the device to sequentially bring each discrete dose of medicament carried by each blister pocket of the strip to an opening station. Such devices typically comprise protective cover, which encloses the mouthpiece when the device is not in use, coupled to a cover drive mechanism. The cover drive mechanism is in turn coupled to a strip advancement mechanism (e.g. via a gear train).

During the actuation of the device, the cover drive mechanism is actuated by the patient opening the protective cover. This action engages the internal drive mechanism which peels the blister strip to allow for exposure of the medicament from a blister pocket to the patient. The patient then closes the protective cover, which resets the cover drive mechanism but disengages from the internal drive to ensure the internal mechanism is only driven forwards.

However, a problem with this mechanism is the management of the blister strip if the patient does not fully open the cover each time the device is used. The mechanism being misused in this way may leave a partially opened blister pocket, which would leave the medicament open to the atmosphere. Additionally, this may cause the cover drive mechanism to become out of sync with the protective cover, so the blister pocket may not be in correct registration with the mouthpiece. In both scenarios, the delivery and efficacy of the medicament delivery to patient may be impeded.

Hence, there remains a need for improved cover drive mechanisms which ensure correct and consistent registration of the blister pockets, regardless of any misuse of the device such as partially opening and closing the protective cover, any number of times. It is an object of the invention to address at least one of the above problems, or another problem associated with the prior art.

SUMMARY OF THE INVENTION

A first aspect of the invention provides a medicament dispenser for use with at least one medicament carrier carrying multiple distinct medicament dose portions. The medicament dispenser comprises: (a) a dispensing mechanism actuable for dispensing the dose portions carried by the at least one medicament carrier; (b) a mouthpiece; and (c) a cover for the mouthpiece, the cover being movably mounted to the dispenser for sequential movement from a closed position in which the mouthpiece is at least partially covered, to an open position in which the mouthpiece is uncovered, via a first position, and optionally via a second position between the first position and the closed position that includes the closed position.

The cover is adapted to couple with the dispensing mechanism such that movement of the cover from the closed position to the open position via the first position results in actuation of the dispensing mechanism. The cover is also adapted to couple with the dispensing mechanism such that movement of the cover from the closed position to the first position results in partial actuation of the dispensing mechanism; movement of the cover from the first position to the second position does not result in actuation of the dispensing mechanism (or resetting or partial return of the dispensing mechanism); and movement of the cover from the second position towards the open position for a distance equal to the distance between the second and open positions less the distance between the first and second positions results in actuation of the dispensing mechanism, but any further movement of the cover to the open position does not result in actuation of the dispensing mechanism.

In this way, if the cover is not moved the whole way from the closed position to the open position, but is at some point moved backwards to the first position towards the closed position (or even all the way back to the closed position), this backwards movement does not result in any further actuation of the medicament dispenser. However, any forward movement from the first position re-engages the cover with the dispensing mechanism.

The cover may be moved backwards and forwards any number of times between the closed position and the open position. However, once the cover has moved forward by a total distance equal to the distance between the closed position and the open position, this results in actuation of the dispensing mechanism. Thus, any further movement of the cover to the open position once the dispensing mechanism has been actuated does not result in any further actuation of the medicament dispenser, and as such this further movement of the cover to the open position is referred to as "lost motion".

In some embodiments, the medicament dispenser may comprise: a rotation control member; a driving plate, to drive stepwise advancement of the dose portions to the dispensing mechanism for inhalation by a patient at an actuated position of the driving plate, the driving plate comprising a camming feature and ratchet teeth; and a body comprising a slot.

Suitably, the rotation control member may be driven between a rest state and an actuated state via an intermediate state by respective reciprocal movement of the cover between the closed position and the open position, for example via one or more intermediate positions. The driving plate may be mounted for reciprocal movement between a disengagement plane and an engagement plane. The camming feature and slot may together be arranged to allow the driving gear to be moved reciprocally between the disengagement plane and the engagement plane. For example, when the rotation control member moves from the rest state to the intermediate state, the rotation control member may be arranged to engage with the camming feature such that that camming feature engages with the slot to move the driving plate from its disengagement plane to its engagement plane.

Suitably, movement of the rotation control member in the intermediate state towards the actuated state may be arranged to always engage the rotation control member with one of the camming feature or the ratchet teeth to move the driving plate. Movement of the rotation control member in the intermediate state towards the actuated state may move the driving plate in the engagement plane towards its actuated position.

Suitably, movement of the rotation control member in the intermediate state away from the actuated state may be arranged to disengage the rotation control member from the driving plate, for example such that the driving plate remains stationary (i.e. it is not moved backwards in the engagement plane away from its actuated position). Movement of the rotation control member in the intermediate state towards the actuated state may suitably be arranged to always engage the rotation control member with one of the camming feature or the ratchet teeth to move the driving plate, such that the driving plate is rotatable in a single direction (i.e. the drive direction) to its actuated state to drive stepwise advancement of the dose portions.

In some embodiments, when the rotation control member moves from the rest state to the intermediate state, the rotation control member may urge the camming feature against an inclined wall of the slot to move the driving plate from its disengagement plane to its engagement plane.

In such embodiments, when the rotation control member is in its rest state, the rotation control member may be biased against the camming feature.

In some embodiments, the body may comprise comprises a second slot. In such embodiments, when the rotation control member moves from the intermediate to the actuated state, the rotation control feature may move the camming feature into the second slot to move the driving plate from its engagement plane to its disengagement plane.

Suitably, the second slot may have a wall directed transverse to the engagement plane such as to provide a cliff edge for the camming feature as it is urged round. In this way, the camming feature may pass into the second slot when control member moves from the intermediate state to the actuated state. For example, the camming feature may pass abruptly into the second slot when control member moves from the intermediate state to the actuated state. Suitably, both the first and second slots may have a wall directed transverse to the engagement plane such as to provide a cliff edge for the camming feature as it is urged round.

In some embodiments, the driving plate may be biased towards the disengagement plane.

In some embodiments, the driving plate may comprise an annulus connected to a central shaft by one or more flexible legs.

In some embodiments, movement of the driving plate in a direction opposite to the drive direction may be prevented by means of a ratchet. The ratchet may comprise a spring that releases when the driving plate moves in the drive direction and tightens when the driving plate moves the direction opposite to the drive direction to prevent movement of the driving plate in the direction opposite to the drive direction In some embodiments, the rotation control member and the driving plate may be mounted about a common axis.

In some embodiments, the rotation control member may comprise at least one flexible arm extending generally circularly. For example, the rotation control member may comprise at least one flexible arm extending in a circular arc. Suitably, the rotation control member may comprise a number of flexible arms equal in number to the number of slots in the body. The at least one flexible arm may conveniently be arranged to engage the camming feature or ratchet teeth to move the driving plate.

In some embodiments, the rotation control member may comprise three flexible arms.

In some embodiments, the camming feature may extend radially outwardly from the annulus of the driving plate. For example, the camming feature may be arranged on a protrusion extending radially outwardly from the annulus of the driving plate. Suitably, the camming feature may have an angled surface extending in a circumferential direction.

In such embodiments, the driving plate may be rotatable in an anticlockwise direction, when viewed from the rotation control member. Suitably, the angled surface of the camming feature may extend in the anticlockwise direction, for example, such that the angled surface is directed generally towards the rotation control member in the anticlockwise direction.

Suitably, in its closed position, the cover may be in position in which it cannot be moved to cover the mouthpiece of the inhaler any further. Suitably, in the open position, the cover may be in a position in which it cannot be moved to any further away from the mouthpiece of the medicament dispenser.

In some embodiments, the medicament dispenser may be a dry powder inhaler (DPI).

In some embodiments, the at least one medicament carrier may comprise a blister strip comprising one or more discrete medicament dose portions. The one or more dose portions may comprise medicament powder and/or a medicament in tablet form.

A second aspect of the invention provides medicament dispenser comprising: a patient manual interface; a rotation control member; a driving plate, to drive stepwise advancement of medicament dose portions to a dispensing mechanism for inhalation by a patient at an actuated position of the driving plate, the driving plate comprising a camming feature and ratchet teeth; and a body comprising a slot.

The rotation control member is driven between a rest state and an actuated state via an intermediate state by respective reciprocal movement of the patient manual interface between a rest state and an actuated state, for example via an intermediate state. The driving plate is mounted for reciprocal movement between a disengagement plane and an engagement plane, the camming feature and slot together allowing the driving plate to be moved reciprocally between the disengagement plane and the engagement plane. When the rotation control member moves from the rest state to the intermediate state, the rotation control member engages with the camming feature (i.e. such that that camming feature engages with the slot) to move the driving plate from its disengagement plane to its engagement plane.

Movement of the rotation control member in the intermediate state away from the actuated state is arranged to disengage the rotation control member from the driving plate such that the driving plate remains stationary. Movement of the rotation control member in the intermediate state towards the actuated state is arranged to always engage the rotation control member with one of the camming feature or the ratchet teeth to move the driving plate, such that the driving plate is rotatable in a single direction (i.e. the drive direction) to drive stepwise advancement of the dose portions.

Suitably, movement of the rotation control member in the intermediate state towards the actuated state may be arranged to always engage the rotation control member with one of the camming feature or the ratchet teeth to move the driving plate. Movement of the rotation control member in the intermediate state towards the actuated state may move the driving plate in the engagement plane towards its actuated position.

In some embodiments, the patient manual interface may comprise a cover. For example, the patient manual interface may comprise a cover for a mouthpiece of the medicament dispenser. Suitably, the cover may be movably mounted to the dispenser for sequential movement from the rest state in which the mouthpiece is at least partially covered, to an actuated state in which the mouthpiece is uncovered.

The various embodiments described above in relation to the first aspect of the invention also apply mutatis mutandis to the second aspect of the invention.

Throughout the description and claims of this specification, the words "comprise" and "contain" and variations of the words, for example "comprising" and "comprises", mean "including but not limited to", and do not exclude other components, integers or steps. Moreover, the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible.

BRIEF DESCRIPTION OF THE DRAWINGS

One or more embodiments of the invention will now be described, by way of example only, with reference to the accompanying drawings, in which.

DETAILED DESCRIPTION

Figure 1:
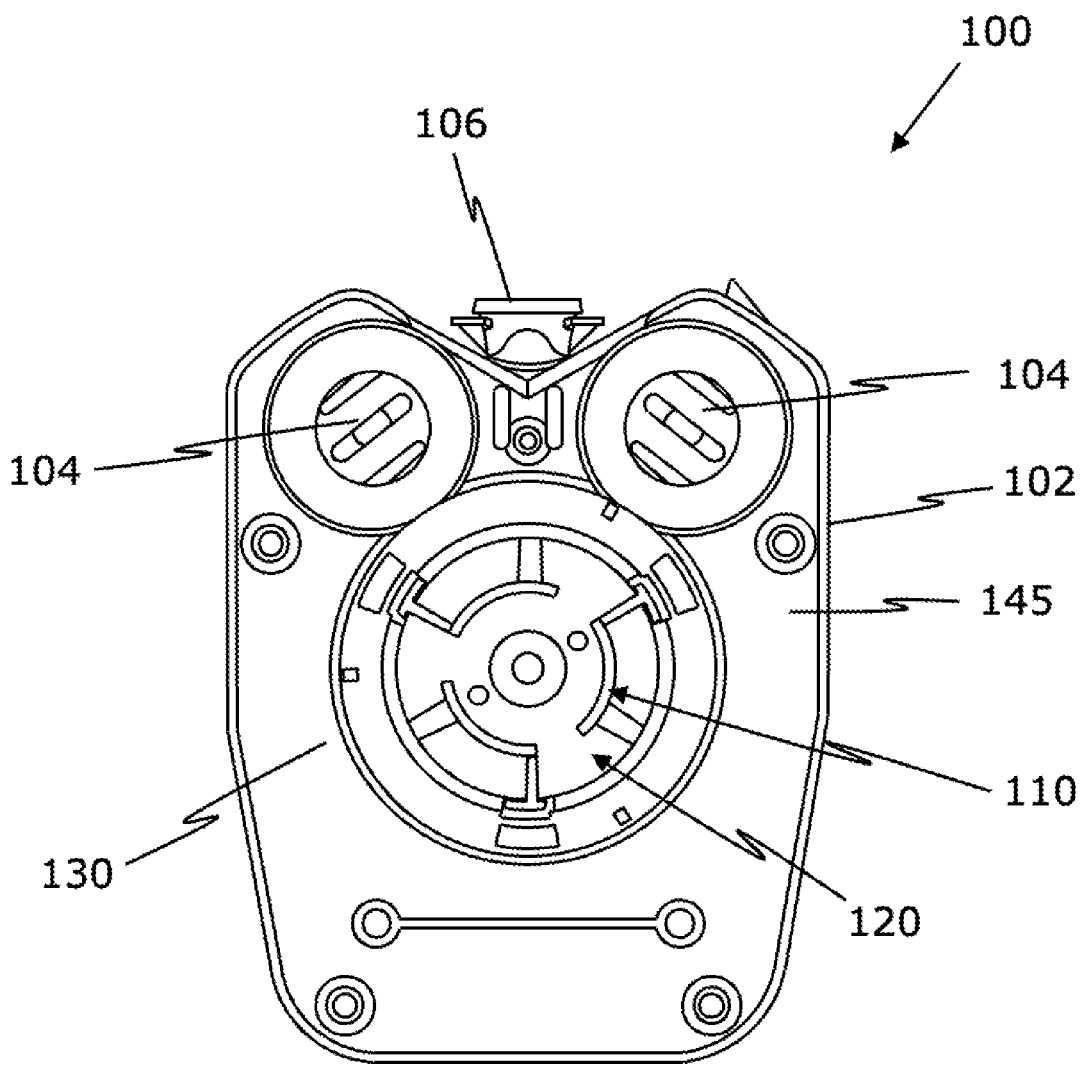
FIG. 1 is a side view of a dry powder inhaler in accordance with a first embodiment of the invention.

Referring to FIG. 1, a dry powder inhaler 100 according to a first embodiment of the invention comprises a housing 102, which contains a supply of medicament (not visible in FIG. 1). In this example, the supply of medicament is in the form of a blister strip defining discrete dose portions of a dry powder medicament. The housing 102 comprises a pair of spindles 104, which form part of a dispensing station (not visible in FIG. 1) contained within the housing 102. The dispensing station enables dry powder medicament to be released from the dose portions of the blister strip in a stepwise manner. The dry powder inhaler 100 also comprises a manifold 106 inserted into an upper portion of the housing 102. The manifold 106 enables dry powder medicament released from the dose portions to be inhaled into the lungs of a user of the inhaler 100 through a mouthpiece (not shown in FIG. 1).

The dry powder inhaler 100 further comprises a driving plate 110, which drives a mechanism (not shown) in the dispensing station for releasing dry powder medicament from the dose portions of the blister strip in a stepwise fashion. A rotation control member 120 sits above the driving plate 110 with respect to the housing 102. The driving plate 110 sits within a circular opening of a body 130, which is attached to a face of the housing 102. The rotation control member 120 sits above the driving plate 110.

The dry powder inhaler 100 further comprises a cover (not shown) attached to the rotation control member 120, which is moveable through 120° from a first fully closed (i.e. rest) position in which it covers the manifold 106 to a second fully open (i.e. actuated) position in which it does not cover the manifold 106. The cover prevents dirt from entering the manifold 106 when the dry powder inhaler 100 is not in use. Reciprocal 120° movement of the cover from the first (fully closed) position to the second (fully open) position and from the second (fully open) position back to the first (fully closed) position rotates the rotation control member 120 anticlockwise and clockwise respectively through 120°.

Figure 2:
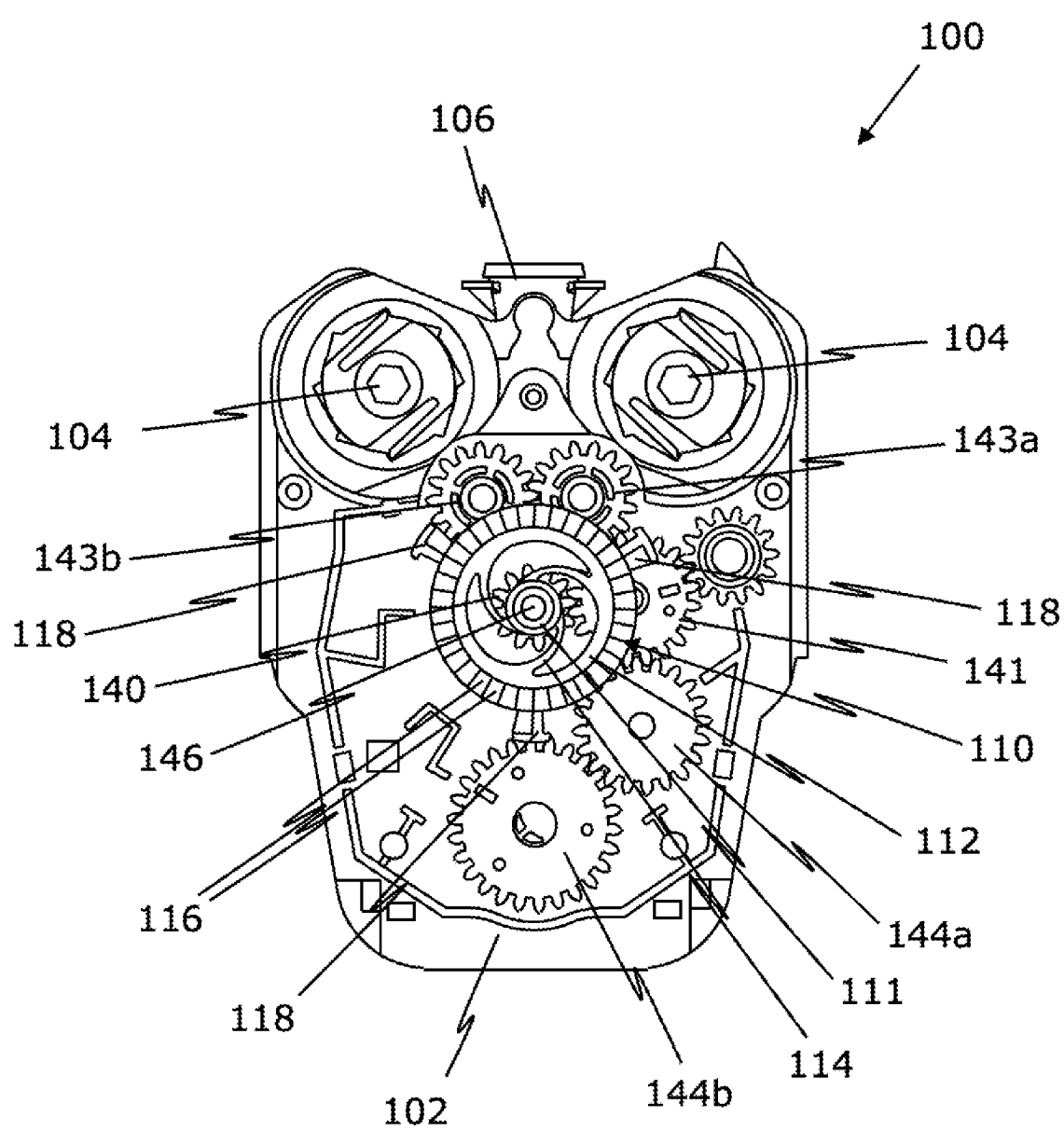
FIG. 2 is a side view of the dry powder inhaler of FIG. 1 in which the rotation control member and body have been removed.
Figure 3:
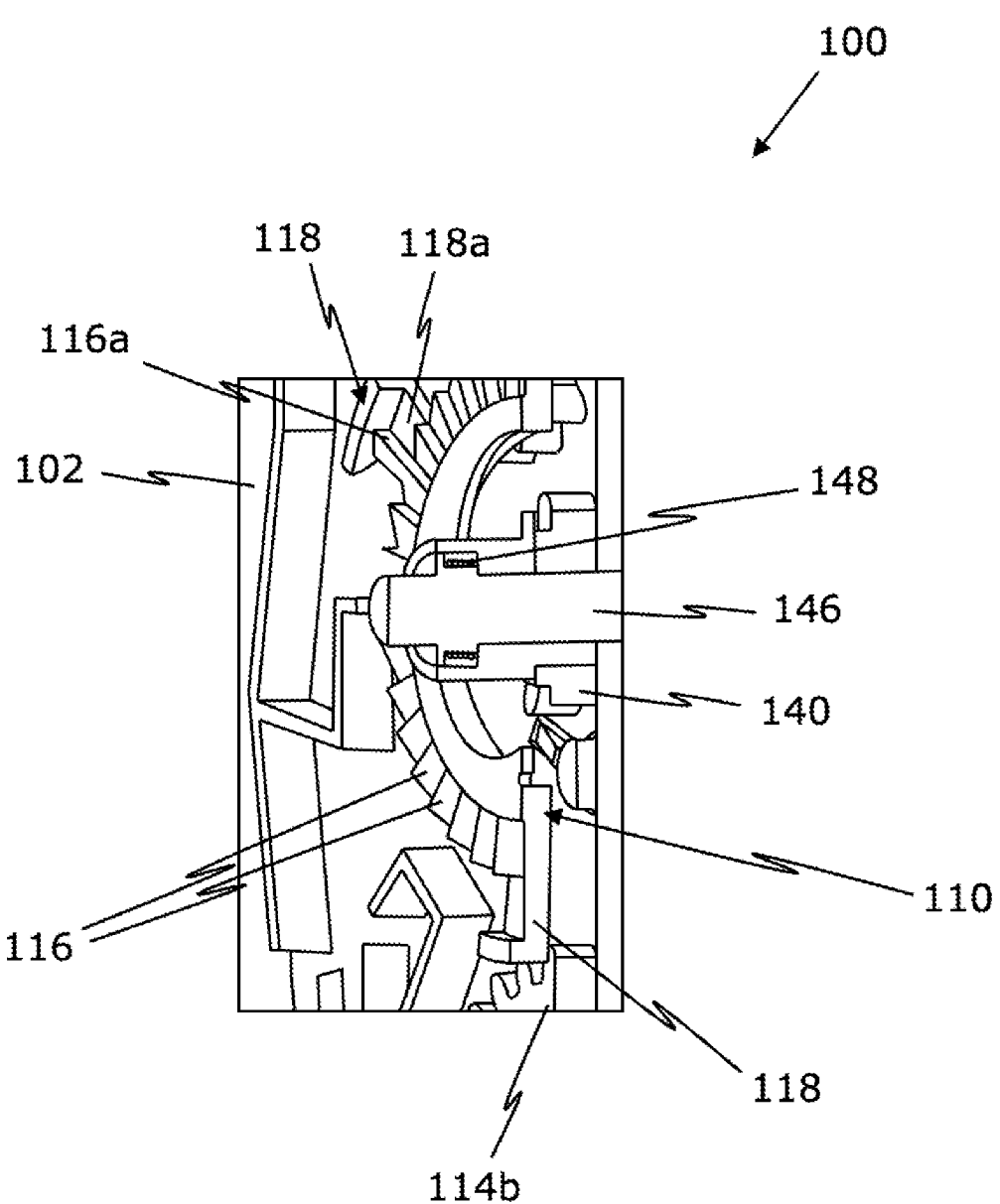
FIG. 3 is a perspective cross sectional view of the driving plate of the dry powder inhaler of FIG. 1.

FIGS. 2 and 3 show views of the dry powder inhaler 100 of FIG. 1, in which the rotation control member 120 and body 130 have been removed to show the driving plate 110 and underlying gear mechanism. A primary gear 140 is arranged on the underside of the driving plate 110 is aligned and driven by the driving plate 110. The primary gear 140 connects to an idler gear 141, which in turn is connected to gears 143*a* and 144*a*. Gear 143*a* connects to gear 143*b*. Gear 144*a* connects to gear 144*b*. Gears 143*a*, 143*b*, 144*a*, 144*b* connect to the dispensing station contained within the housing 102 and control the release of dry powder medicament in a stepwise fashion from the portions of the blister strip and spooling of waste blisters. The driving plate 110 and primary gear 140 are rotatable about a spindle 146, which protrudes upwardly from the housing 102.

The driving plate 110 comprises an inner circumferential ring 111 which is attached to an outer circumferential ring 112 by three equally spaced apart curved arms 114. A series of ratchet teeth 116 run in a continuous loop around the circumference of an upper side of the outer circumferential ring 112. Three equally spaced apart skis 118 extend radially outward from the outer circumferential ring 112. As can be seen in FIG. 3, each ski 118 comprises an extended ratchet tooth 116*a* that extends beyond the outer circumferential ring 112, and a recess 118*a* located behind the portion of the extended ratchet tooth 116*a* extending past the outer circumferential ring 112.

The driving plate 110 is secured on the spindle 146. A spring 148 (visible only in FIG. 3) arranged between the spindle 146 and the driving plate 110 acts as a ratchet due to the spring 148 binding to the spindle 146 on clockwise (i.e. reverse) rotation. Due to the binding action of the spring 148, the rotation control member 120 can be rotated backwards clockwise without causing any rotation of the driving plate 110.

Figure 4:
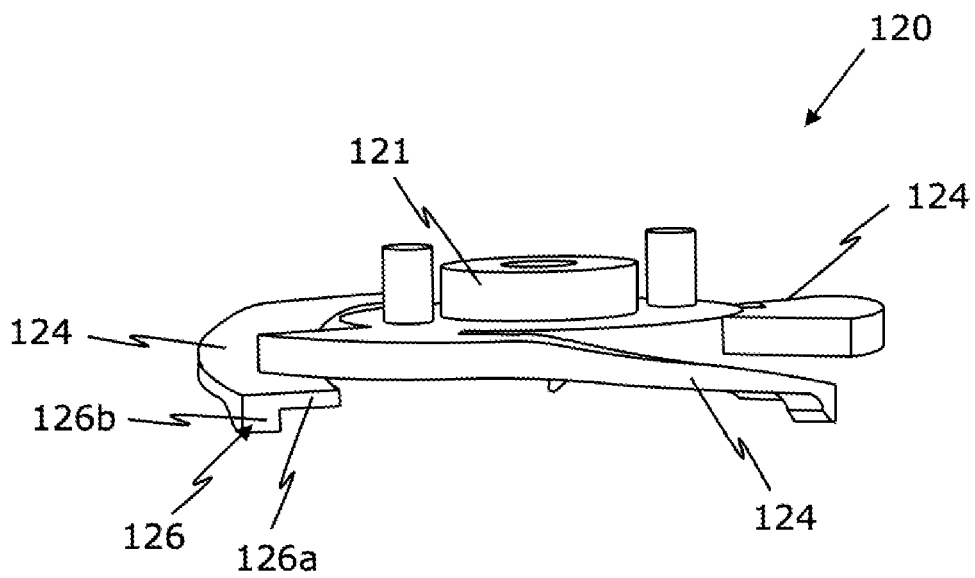
FIG. 4 is a front view of the rotation control member of the embodiment of FIG. 1.

Referring to FIG. 4, the rotation control member 120 comprises a cylindrical core 121 having a central aperture for receiving the spindle 146. Three equally spaced apart curved flexible arms 124 extend radially outward from the cylindrical core 121 and are angled downwardly below the plane of the cylindrical core 121. The end of each of the flexible arms 124 defines an engagement face 126 for engaging with the ratchet teeth 116 of the driving plate 110. Each engagement face 126 is asymmetric in profile having a horizontal portion 126*a* and a radially outward vertical portion 126*b*.

Figure 5:
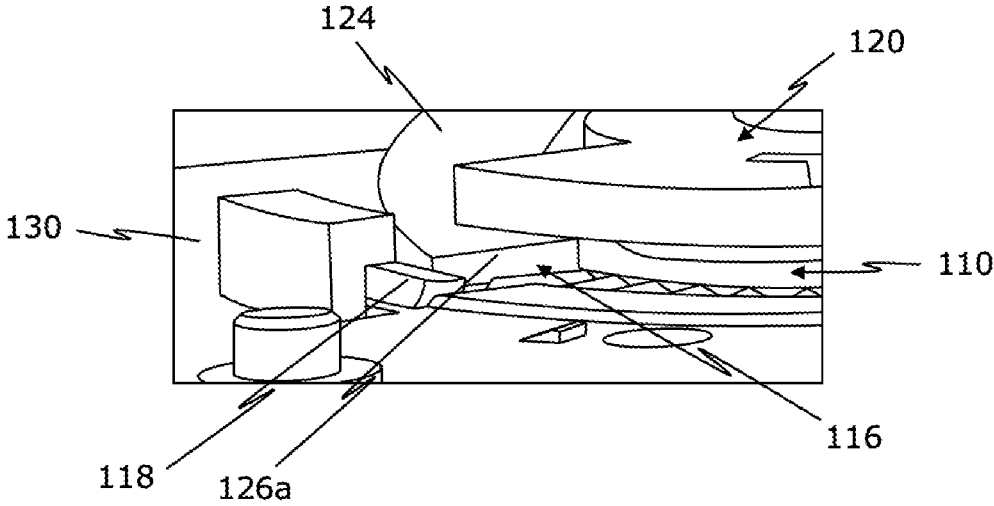
FIG. 5 is a perspective view of the driving plate, rotation control member and body of the embodiment of FIG. 1.
Figure 6:
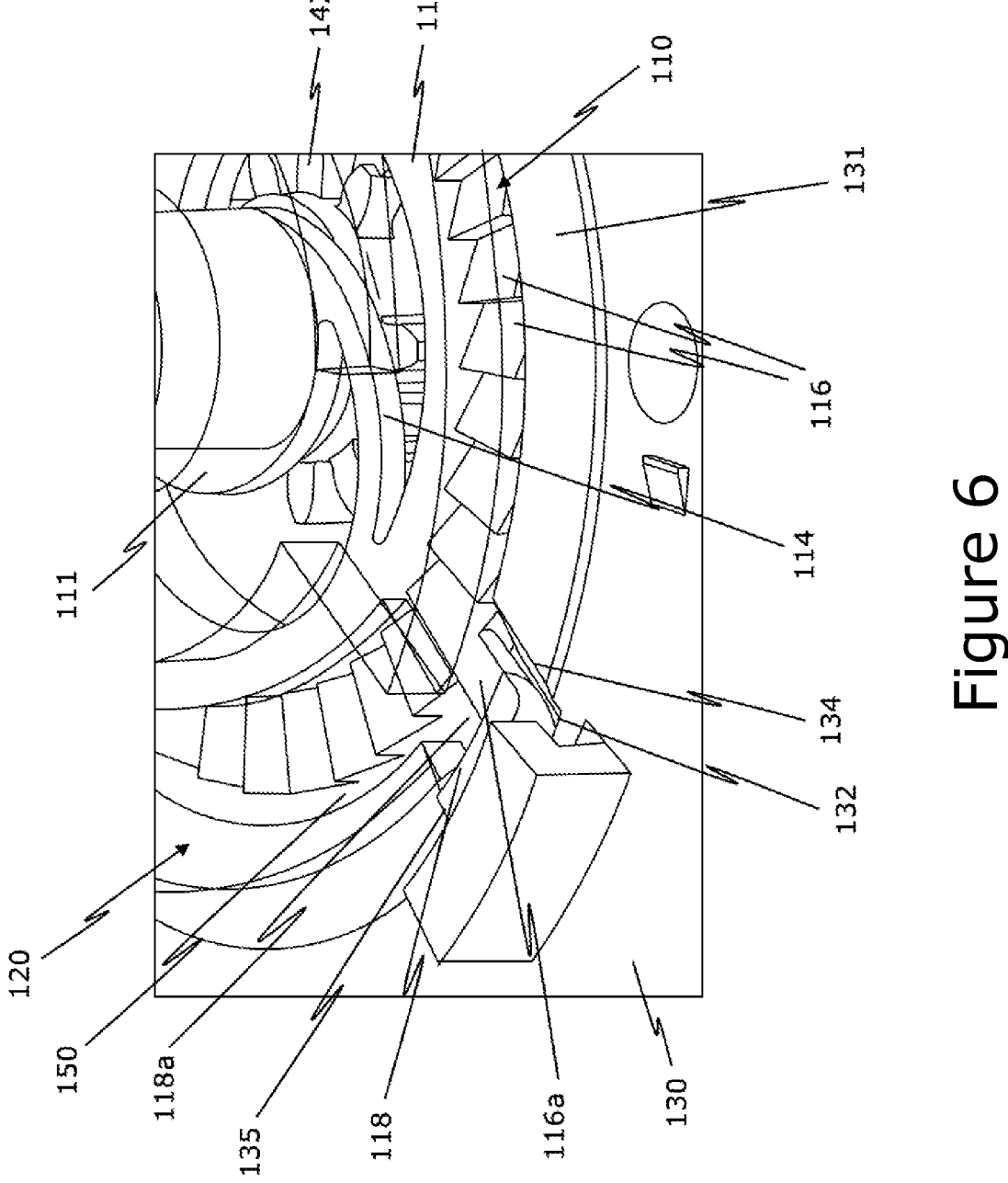
FIG. 6 is an alternative perspective view of the driving plate, rotation control member and body of FIG. 5.

FIGS. 5 and 6 show perspective views of the assembly of the driving plate 110, rotation control member 120 and body 130 of FIG. 1, wherein the driving plate 110 is in the first (disengagement) plane. The driving plate 110 sits within the circular opening of body 130, with the rotation control member 120 arranged such that it sits above the driving plate 110 with respect to the housing 102. As can be seen from FIG. 6, a gap 150 runs circumferentially around the driving plate 110, between the driving plate 110 and the opening of the body 130.

In FIGS. 5 and 6, the vertical portions 126*b* of the engagement faces 126 at the end of each of the flexible arms 124 of the rotation control member 120 are shown located in the recesses 118*a* of the skis 118, abutting the extended ratchet teeth 116*a* of the skis 118. In this configuration, the horizontal portions 126*a* of the engagement faces 126 lie above the plane of the driving plate 110.

In FIG. 6, the rotation control member 120 is shown as transparent. As can be seen from FIG. 6, the body 130 comprises three slots 132 spaced apart at equal distances at the edge of the circular opening of the body 130. The slots 132 are sized to accommodate the skis 118 of the driving plate 110. As the slots 132 are equally spaced apart, if one ski 118 is accommodated in a slot 132, the other two skis 118 will also be accommodated in the two other slots 132. In this way, all three skis 118 are always accommodated in all three slots 132 at the same time. When the skis 118 are accommodated in the slots 132, the skis 118 are in the in the first (disengagement) plane. Each slot 132 has a ramp 134 in the forward circumferential direction of rotation of the driving plate 110 and vertical wall 135 in the rear direction. In this embodiment, the forward circumferential direction of rotation of the driving plate 110 is anticlockwise as viewed from above with respect to the housing 102.

Figure 7:
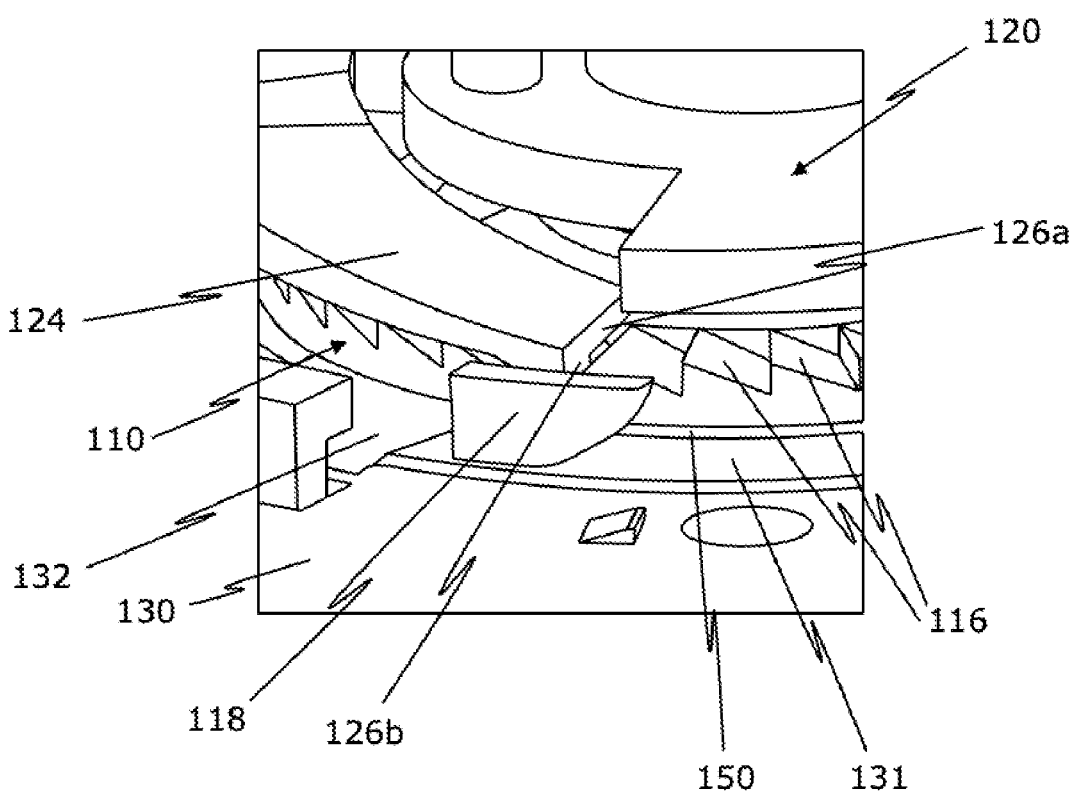
FIG. 7 is a perspective view of the rotation control member, driving plate and body of FIGS. 5 and 6 after the rotation control member has started to rotate anticlockwise and the driving plate has been moved into the engagement plane.
Figure 8:
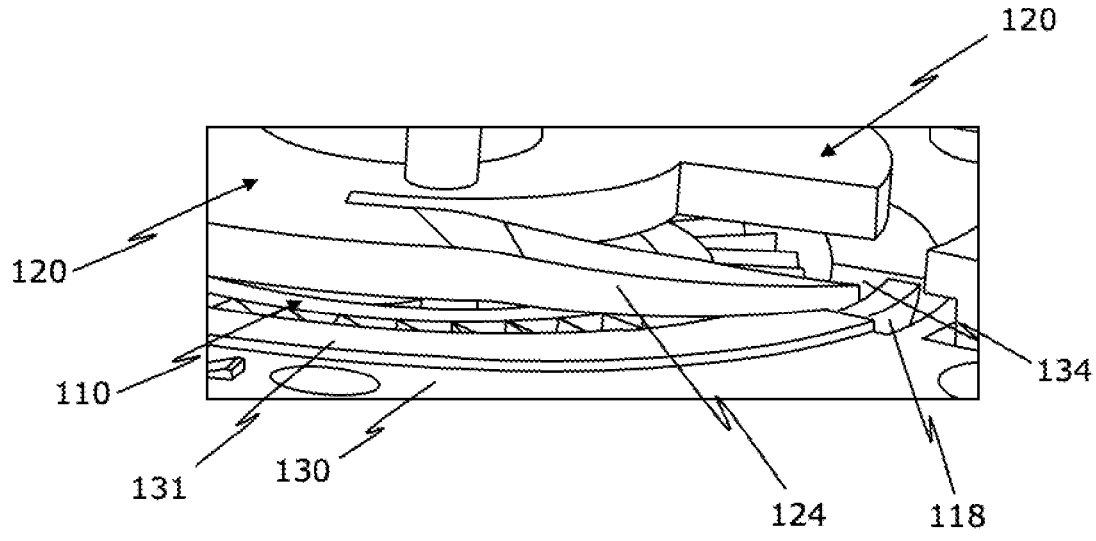
FIG. 8 is a perspective view of the rotation control member, driving plate and body of FIG. 7 after the rotation control member has been rotated anticlockwise by 120° and the driving plate has moved back into the disengagement plane in the next slot along.
Figure 9:
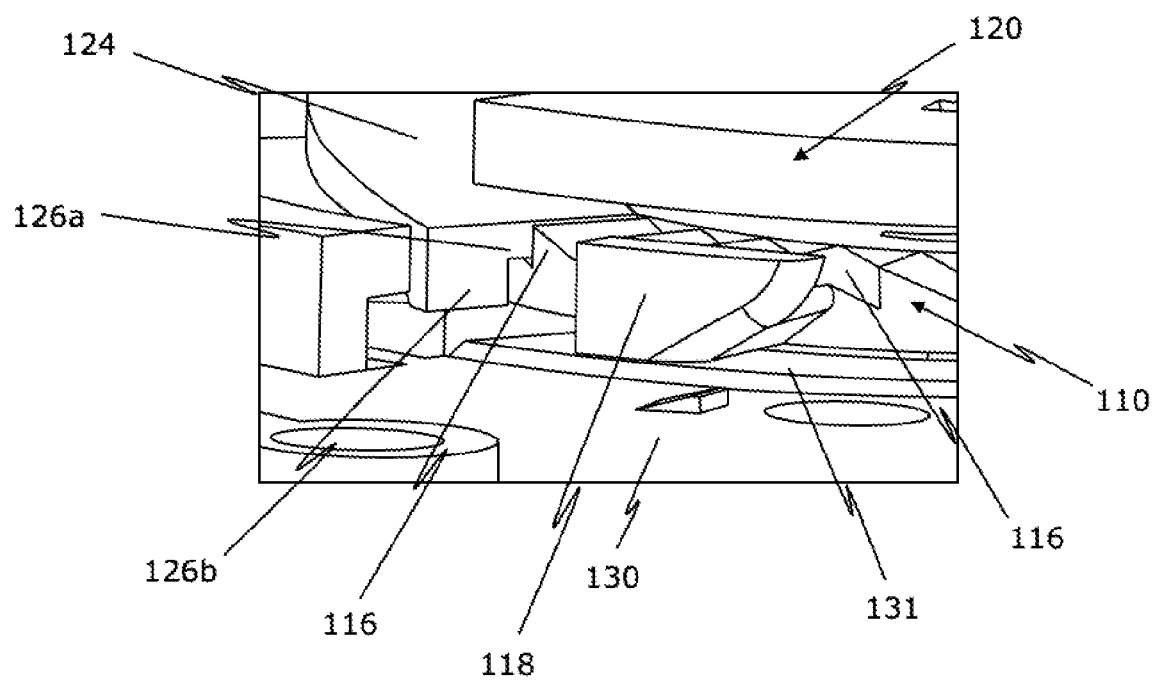
FIG. 9 is a perspective view of the rotation control member, driving plate and body of FIGS. 5 and 6 after the rotation control member has started to rotate anticlockwise and the driving plate has been moved into the engagement plane, and the driving control member has subsequently been rotated backwards in the clockwise direction so that it is in engagement with a tooth of the ratchet teeth.
Figure 10:
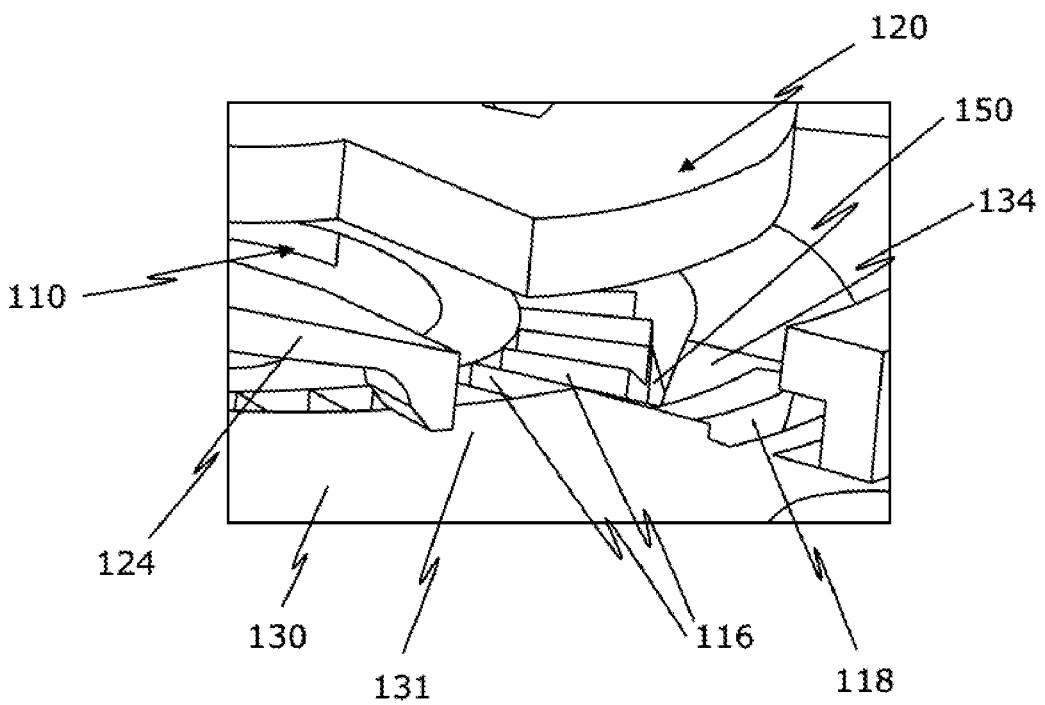
FIG. 10 is a perspective view of the rotation control member, driving plate and body of FIG. 9 after the rotation control member has been rotated anticlockwise by a total of 120° and the driving plate has moved back into the disengagement plane in the next slot along.

Referring now to FIGS. 6 to 8, in use, initially the cover is in the first (fully closed) position in which it covers the manifold 106 and mouthpiece (not shown in FIGS. 6 to 8). When the cover is in the first (fully closed) position, the driving plate 110 is in the first (disengagement) plane as shown in FIG. 6, wherein the skis 118 are accommodated in the slots 132 of the body 130. Movement of the cover by a user through 120°, from the first (fully closed) position in which it covers the manifold 106 to the second (fully open) position in which it does not cover the manifold 106, rotates the rotation control member 120 anticlockwise through 120°.

As shown in FIG. 7, as the rotation control member 120 starts to rotate anticlockwise, the vertical portions 126*b* of the engagement faces 126 at the end of each of the flexible arms 124 of the rotation control member 120 push the extended ratchet teeth 116*a* of the skis 118, thereby causing the driving plate 110 to rotate anticlockwise. As a result, the skis 118 are pushed up and over the ramps 134 in the slots 132 such that the skis 118 slide over a surface 131 at the top of the body 130 which runs around the circumference of the circular opening in the body 130. This pushes the driving plate 110 from the first (disengagement) plane to the second (engagement) plane.

As the cover is moved through 120°, the driving plate 110 also rotates through 120° until the skis 118 pass over the vertical walls 135 of the next slots 132 along such that they drop into the next slots 132 along as shown in FIG. 8. As the skis 118 drop into the next slots 132 along, the driving plate 110 moves back from the second (engagement) plane back to the first (disengagement) plane. Rotation of the driving plate through 120° also rotates the primary gear 140, which in turn rotates the idler gear 141 and the number of other gears 143*a*, 143*b*, 144*a*, 144*b* through 120°, thereby releasing of a dose of dry powder medicament from a portion of the blister strip in the dispensing station contained within the housing 102. The user can then inhale the released dose of dry powder medicament through the manifold 106.

Once in the second (fully open) position, the cover cannot be physically moved any further open due to the geometry of the dry powder inhaler 100. Therefore, the user can now only return the cover back to towards the first (fully closed) position in which it covers the manifold 106. This rotates the rotation control member 120 back through 120° and thus the vertical portions 126*b* of the engagement faces 126 at the end of each of the flexible arms 124 of the rotation control member 120 now rotate backwards over the body 130 until the flexible arms 124 are returned to the reset position.

The flexibility of the flexible arms 124 allows them to slide over the extended ratchet teeth 116*a* of the rearward skis 118, such that they return to the position shown in FIG. 6, in which the vertical portions 126b of the engagement faces 126 at the end of each of the flexible arms 124 of the rotation control member 120 are shown located in the recess 118a and abutting the extended ratchet teeth 116a of the skis 118. Thus, the cover can then be returned from the second (fully open) position back to the first (fully closed) position without causing any further rotation of the driving plate 110. Movement of the cover by a user through 120° from the first (fully closed) position in which it covers the manifold 106 back to the second (fully open) position in which it does not cover the manifold 106 then causes the process above to repeat, to release a further dose of dry powder medicament from a portion of the blister strip in the dispensing station contained within the housing 102.

In a misuse scenario when the user moves the cover anticlockwise from the first (fully closed) position by only a part of the 120° towards the second (fully open) position, for example say 60° towards the second (fully open) position, and then returns the cover clockwise back to the first (fully closed) position, a dose of dry powder medicament would not be released from a portion of the blister strip in the dispensing station contained within the housing 102 (i.e. the dry powder inhaler 100 would not be actuated).

During rotation of the cover anticlockwise from the first (fully closed) position through 60° to a partially open position, rotation of the rotation control member 120 anticlockwise through 60° would cause the vertical portions 126b of the engagement faces 126 at the end of each of the flexible arms 124 of the rotation control member 120 to push the extended ratchet teeth 116a of the skis 118, thereby causing the skis 118 to move upwards from the first (disengagement) plane to the second (engagement) plane and rotate anticlockwise by 60°.

As the cover is returned clockwise from the second (fully open) position back to the first (fully closed) position, the vertical portions 126b of the engagement faces 126 at the end of each of the flexible arms 124 of the rotation control member 120 would rotate clockwise through 60° flexing and clicking over the ratchet teeth 116 of the driving plate 110.

Whilst the cover is now back in the first (fully closed) position, the driving plate 110 would therefore remain in the same position where it has been rotated only 60° anticlockwise with the skis 118 still in the second (engagement) plane. As the primary gear 140 has only been rotated anticlockwise by 60°, this in turn means the idler gear 141 and the number of other gears 143a, 143b, 144a, 144b, have also only rotated anticlockwise by 60° and thus a dose of dry powder medicament has not yet been released from a portion of the blister strip in the dispensing station contained within the housing 102 (i.e. the dry powder inhaler 100 has not yet been actuated).

However, when the user again moves the cover anticlockwise from the first (fully closed) position back towards the second (fully open) position, the horizontal portions 126a of the engagement faces 126 at the end of each of the flexible arms 124 of the rotation control member 120 now engage the nearest ratchet tooth 116, thereby causing the driving plate 110 to continue rotating anticlockwise. As the cover is moved anticlockwise through the first 60°, the driving plate 110 also rotates anticlockwise through a further 60° until the skis 118 pass over the vertical walls 135 of the next slots 132 along such that they drop into the next slots 132 along. As the skis 118 drop into the next slots 132 along, the driving plate 110 moves back from the second (engagement) plane back to the first (disengagement) plane.

At this point the driving plate 110 has now rotated anticlockwise a full 120°, which means that the primary gear 140 has also rotated anticlockwise a full 120°, which has in turn has rotated the idler gear 141 and the number of other gears 143a, 143b, 144a, 144b, a full 120°, thereby releasing of a dose of dry powder medicament from a portion of the blister strip in the dispensing station contained within the housing. Because the skis 118 have moved downwards back to the first (disengagement) plane, further anticlockwise rotation of the cover to the second (fully open) position (i.e. by a further 60°) simply rotates the vertical portions 126b of the engagement faces 126 at the end of each of the flexible arms 124 of the rotation control member 120 forward by 60° such that they run over the body 130 until they return to the position shown in FIG. 6. Due to this "lost motion" of the driving plate 110, the cover can be moved to the second (fully open) position without releasing a further doses of dry powder medicament.

As the cover is returned clockwise through 120° from the second (fully open) position back to the first (fully closed) position, the vertical portions 126b of the engagement faces 126 at the end of each of the flexible arms 124 of the rotation control member 120 now rotate clockwise over the body 130 until they are returned to the reset position shown in FIG. 6.

Thus, in the misuse scenario, the user may move the cover anticlockwise from the first (fully closed) position by only a part of the 120° towards the second (fully open) position to a part open position, and then can move the cover clockwise to any position between the part open position and the first (fully closed) position without releasing a dose of medicament from a portion of the blister strip in the dispensing station contained within the housing 102 (i.e. without actuating the dry powder inhaler 100). However, any further anticlockwise movement of the cover forward from the part open position towards the second (fully open) re-engages the rotation control member 120 with the driving plate 110, such that a dose of medicament is released once the driving plate 110 has been rotated through a full 120° movement.

Figure 11:
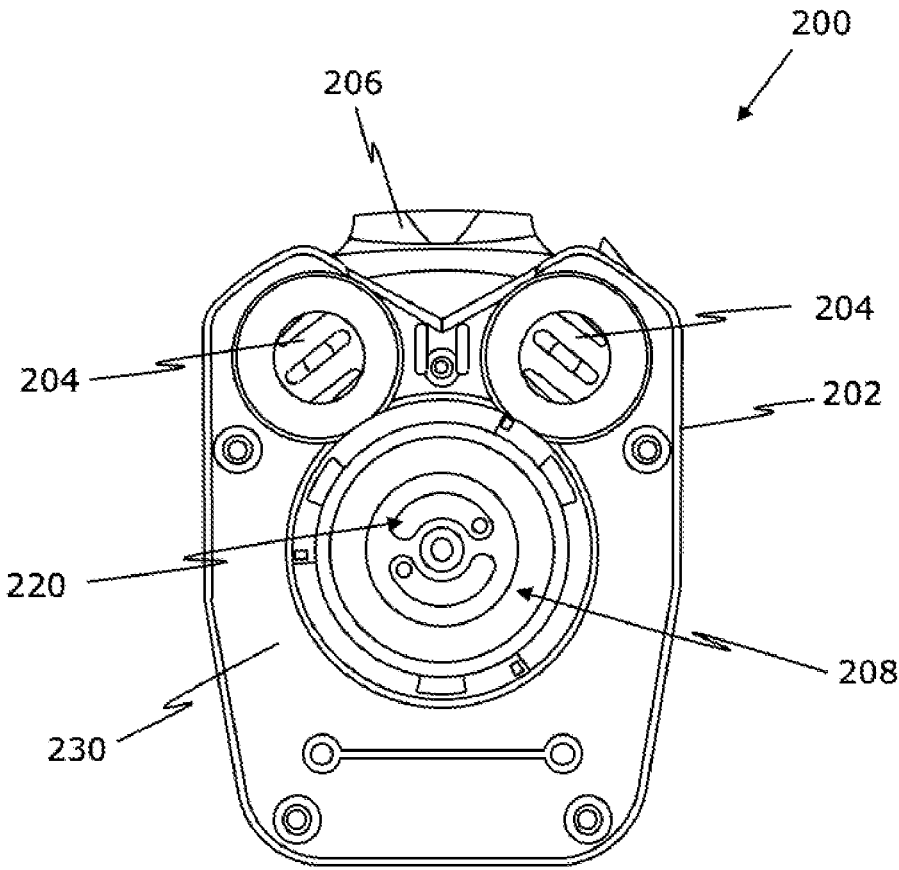
FIG. 11 is a side view of a dry powder inhaler in accordance with a second embodiment of the invention.

Referring to FIG. 11, a dry powder inhaler 200 according to a second embodiment of the invention comprises a housing 202, which contains a supply of medicament (not visible in FIG. 11). In this example, the supply of medicament is in the form of a blister strip defining discrete dose portions of a dry powder medicament. The housing 202 comprises a pair of spindles 204, which form part of a dispensing station (not visible in FIG. 11) contained within the housing 202. The dispensing station enables dry powder medicament to be released from the dose portions of the blister strip in a stepwise manner. The dry powder inhaler 200 also comprises a mouthpiece 206 inserted into an upper portion of the housing 202.

The dry powder inhaler 200 comprises an interface 208, which sits within a circular opening a body 230 attached to a face of the housing 202. The interface 208 sits above and is engaged with a rotation control member 220. The rotation control member 220 sits above and is engaged with a driving plate 210 (not visible in FIG. 11), which drives a mechanism (not shown) in the dispensing station for releasing dry powder medicament from the dose portions of the blister strip in a stepwise fashion.

The dry powder inhaler 200 further comprises a cover (not shown) attached to the interface 208, which is moveable through 120° from a first fully closed (i.e. rest) position in which it covers the mouthpiece 206 to a second fully open (i.e. actuated) position in which it does not cover the mouthpiece 206. The cover prevents dirt from entering the mouthpiece 206 when the dry powder inhaler 200 is not in use. Reciprocal 120° movement of the cover from the first (fully closed) position to the second (fully open) position and from the second (fully open) position back to the first (fully closed) position rotates the interface 208 and rotation control member 220 anticlockwise and clockwise respectively through 120°.

Figure 12:
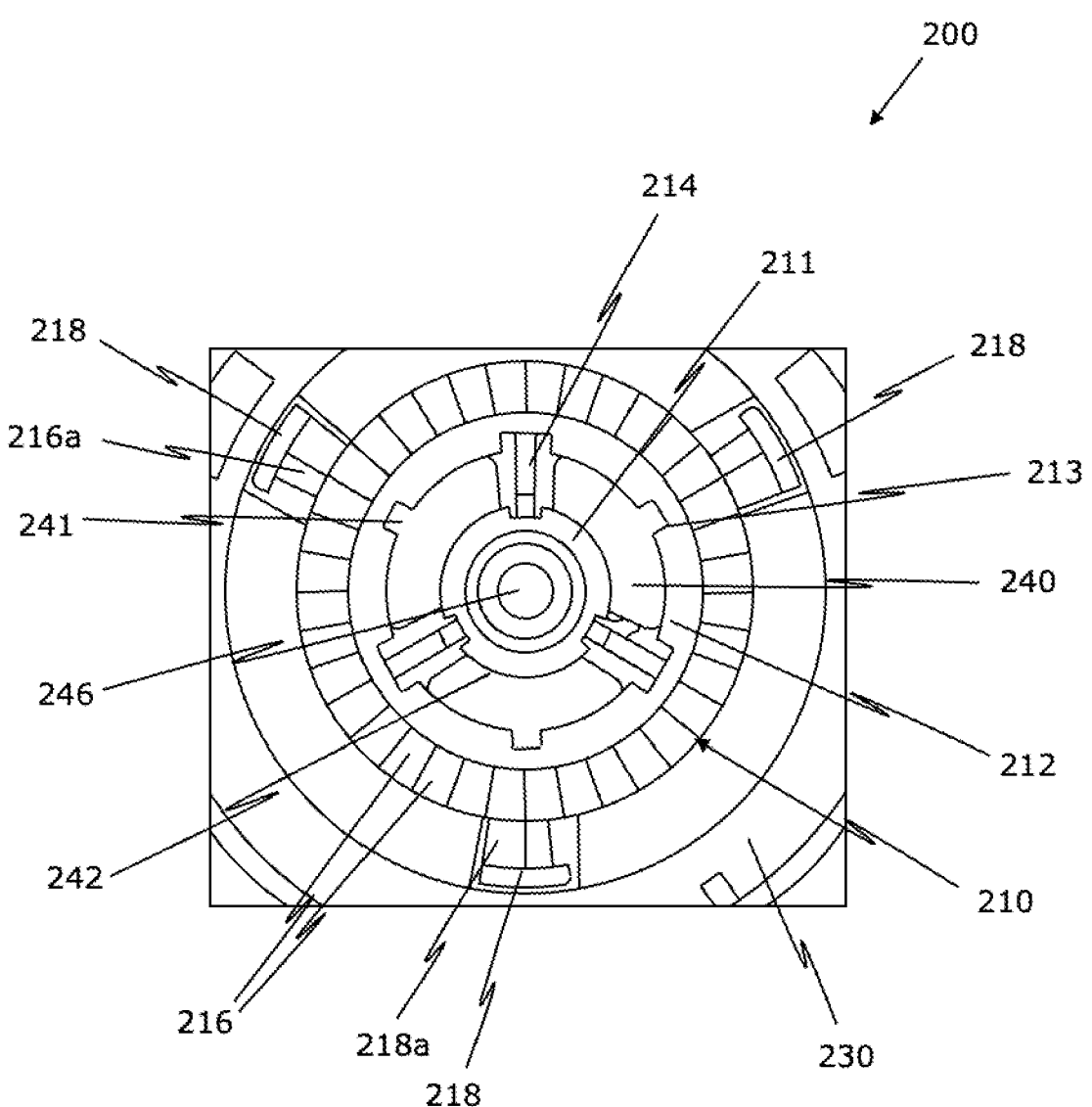
FIG. 12 is a close-up view of the dry powder inhaler of FIG. 11 in which the interface and rotation control member have been removed.

FIG. 12 shows a close-up view of the dry powder inhaler 200 of FIG. 11, in which the interface 208 and rotation control member 220 have been removed to show the underlying driving plate 210. The driving plate 210 comprises an inner circumferential ring 211 which is attached to an outer circumferential ring 212 by three equally spaced apart arms 214. A series of ratchet teeth 216 run in a continuous loop around the circumference of an upper side of the outer circumferential ring 212. Three equally spaced apart skis 218 extend radially outward from the outer circumferential ring 212. Each ski 218 comprises an extended ratchet tooth 216a that extends beyond the outer circumferential ring 212, and a recess 218a located behind the portion of the extended ratchet tooth 216a extending past the outer circumferential ring 212.

A primary drive gear 240 sits within the within the outer circumferential ring 212 of the driving plate 210 and has three equally spaced apart ribs 241 which engage with corresponding slots 213 in the outer circumferential ring 212. The driving plate 210 drives rotation of the primary 240 and is able to move vertically up and down with respect to the primary drive gear 240 by sliding along the ribs 241 of the primary drive gear 240. The primary drive gear 240 also has a circular groove 242 in which the inner circumferential ring 212 of the driving plate 210 sits. The primary drive gear 240 is attached to a spindle 246, which protrudes upwardly from the housing 202. The primary drive gear 240 and driving plate 210 are rotatable about the spindle 246.

Figure 13:
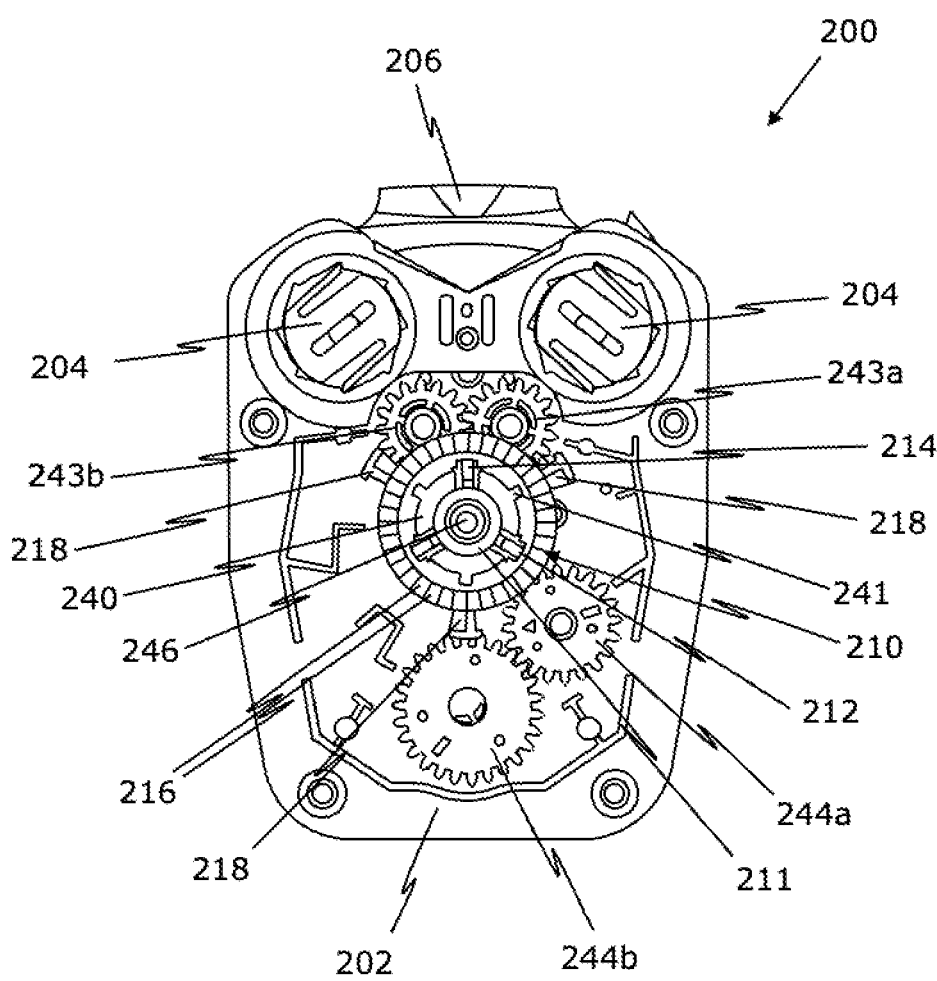
FIG. 13 is a side view of the dry powder inhaler of FIG. 11 in which the interface, rotation control member and body have been removed.
Figure 14:
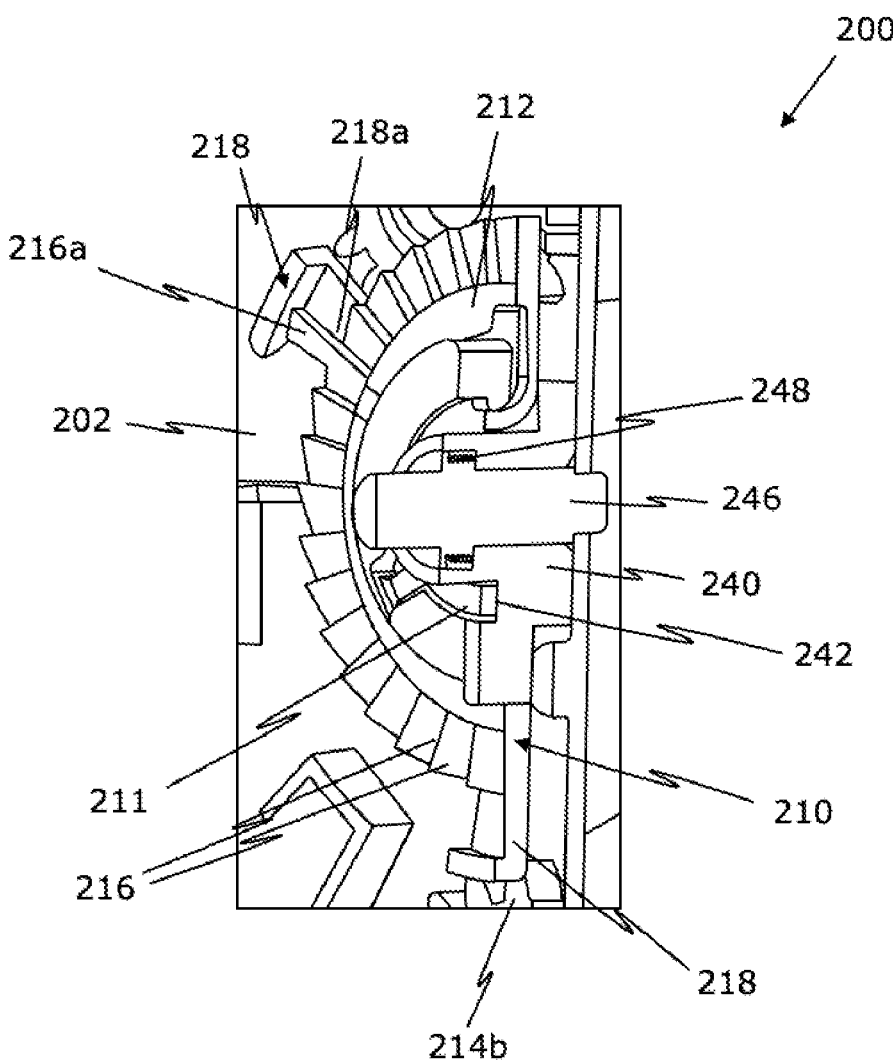
FIG. 14 is a perspective cross sectional view of the driving plate and primary drive gear of the dry powder inhaler of FIG. 11.

FIG. 13 shows a view of the dry powder inhaler 200 of FIG. 11, in which the interface 208, rotation control member 220 and body 230 have all been removed to show the underlying gear mechanism. The primary drive gear 240 connects to an idler gear (not shown), which in turn is connected to a number of other gears 243a, 243b, 244a, 244b, which connect to the dispensing station contained within the housing 202 and control the release of dry powder medicament in a stepwise fashion from the portions of the blister strip and spooling of waste blisters.

The driving plate 210 is secured on the spindle 246. A spring 248 arranged between the spindle 246 and the primary drive gear 240 acts as a ratchet due to the spring 248 binding to the spindle 246 on clockwise (i.e. reverse) rotation. Due to the binding action of the spring 248, the rotation control member 220 can be rotated backwards clockwise without causing any rotation of the driving plate 210 and primary drive gear 240.

Figure 15A:
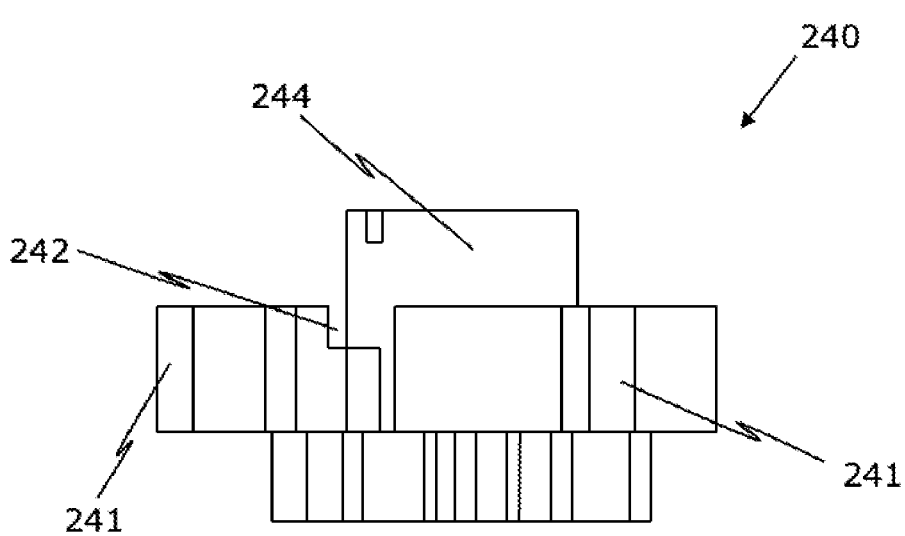
FIG. 15(a) is a side view of the primary drive gear of FIG. 11.
Figure 15B:
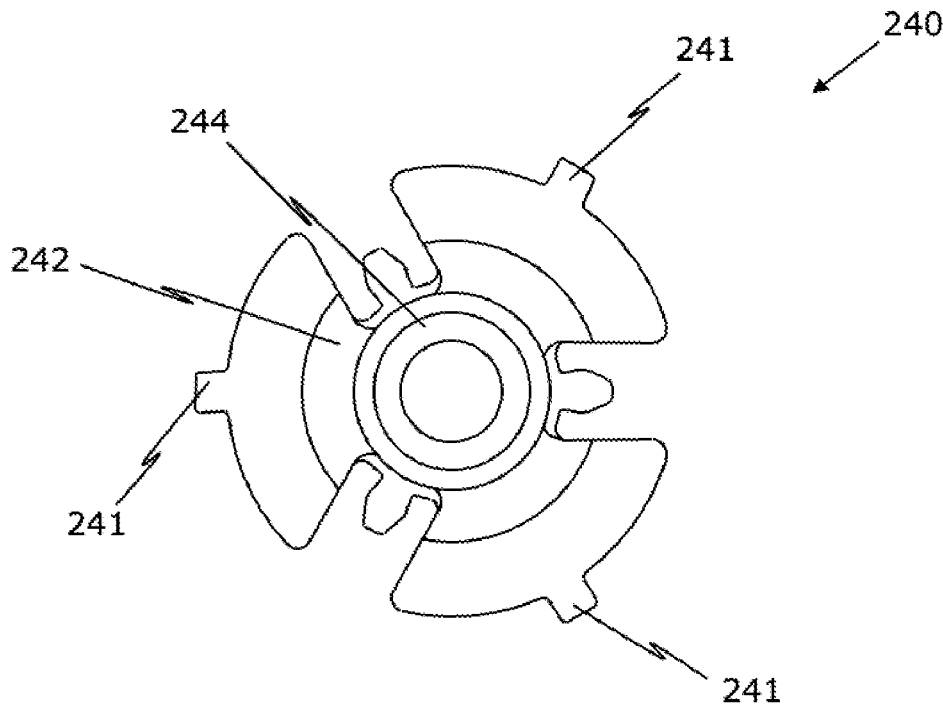
FIG. 15(b) is a plan view of the primary drive gear of FIG. 11.
Figure 16A:
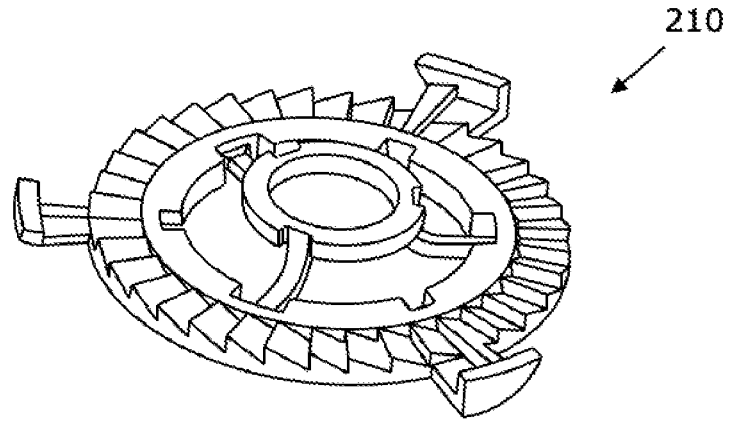
FIG. 16(a) is a side view of the bottom of the driving plate of FIG. 11.
Figure 16B:
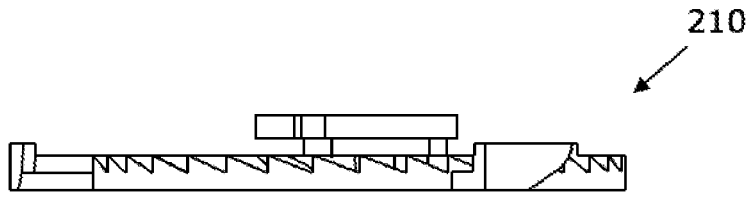
FIG. 16(b) is a side view of the driving plate of FIG. 11.
Figure 16C:
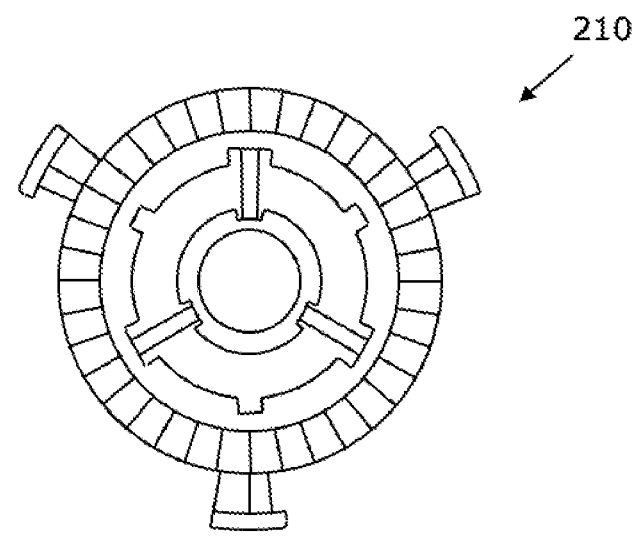
FIG. 16(c) is a plan view of the driving plate of FIG. 11.

Referring to FIGS. 15(a) and (b) the primary drive gear 240 has a central core 244 having a central aperture for receiving the spindle 246. As mentioned above, the primary drive gear 240 has three equally spaced apart ribs 241 for engaging with the slots 213 in the outer circumferential ring 212 of the driving plate 210 and circular groove 242 for receiving the inner circumferential ring 212 of the driving plate 210. FIGS. 16(a) to (c) show various views of the driving plate 210.

Figure 17:
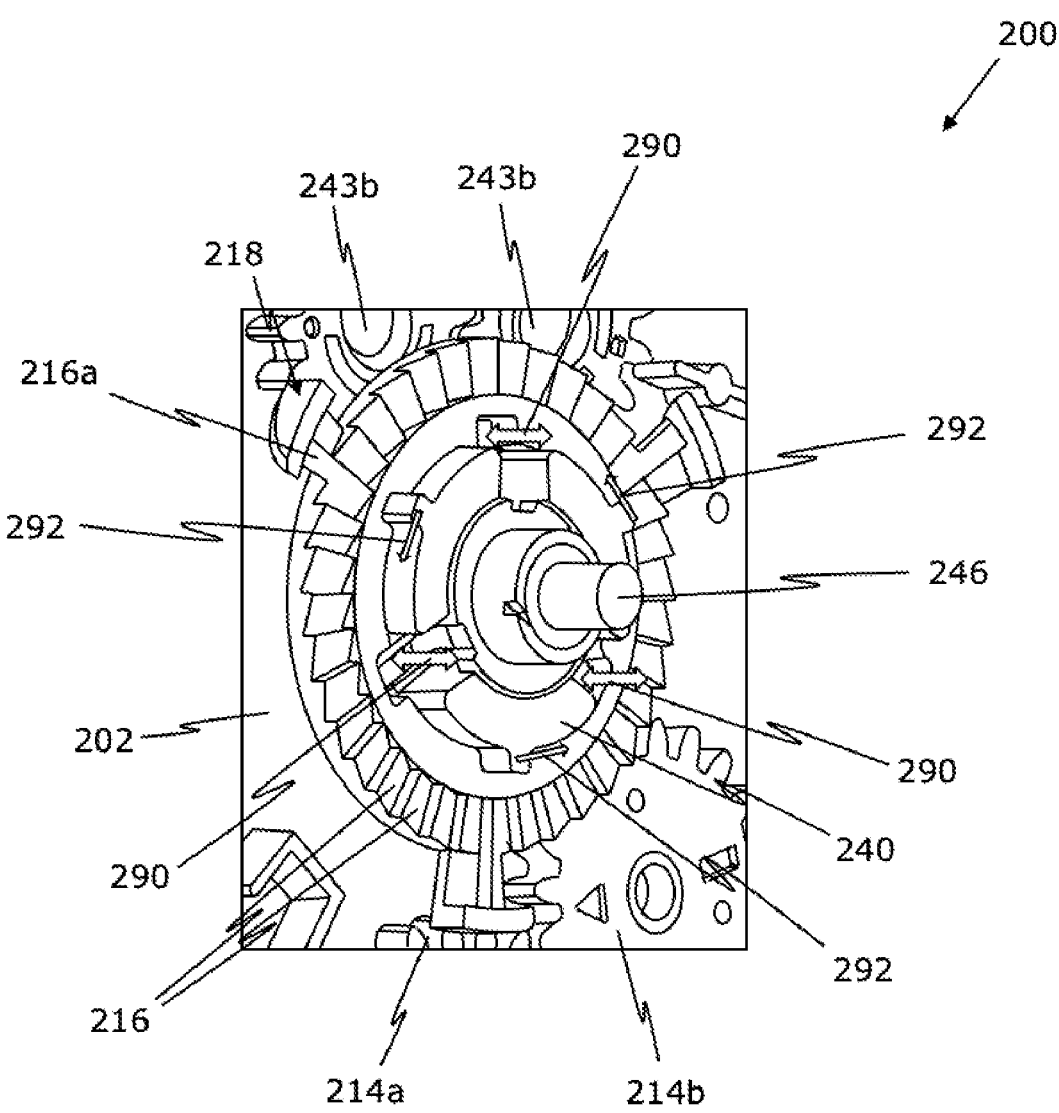
FIG. 17 is a perspective view of the driving plate and primary drive gear of the dry powder inhaler of FIG. 11.

Referring to FIG. 17, as the rotation control member 220 (not shown in FIG. 17) starts to rotate anticlockwise, the rotation control member 220 pushes the extended ratchet teeth 216a of the skis 218, thereby causing the driving plate 210 to rotate anticlockwise. As a result, the skis 218 are pushed up and over ramps in slots of the body 230 (not shown in FIG. 17). This pushes the skis 118 upwards, causing the driving plate 210 to slide upwards along the ribs 241 of the primary drive gear 240 from the first (disengagement) plane to the second (engagement) plane as indicated by the vertical movement arrows 290.

As the cover is moved through 120°, the driving plate 210 also rotates through 120° until the skis 218 pass over vertical walls of the next slots along (not shown in FIG. 17) such that they drop into the next slots along. Rotational movement of the driving plate 210 is transferred to the primary drive gear 240 through the ribs 241 of the primary drive gear 240. As a result, the primary drive gear 240 also rotates through 120° as indicated by the rotational arrows 292. As the skis 218 drop into the next slots along, the driving plate 210 moves back from the second (engagement) plane back to the first (disengagement) plane as indicated by the vertical movement arrows 290. Rotation of the primary drive gear 240 through 120° a rotates the idler gear (not shown) and the number of other gears 243a, 243b, 244a, 244b, through 120°, thereby releasing of a dose of dry powder medicament from a portion of the blister strip in the dispensing station contained within the housing 202. The user can then inhale the released dose of dry powder medicament through the mouthpiece 206.

This arrangement of the driving plate 210 and primary drive gear 240 advantageously reduces the amount of torque applied the driving plate 210 during rotation and movement between the disengagement and engagement phases, which in turn reduces the amount of stress experienced by the driving plate 210. This may prevent the driving plate 210 from bending out of plane or breaking, thereby increasing its useable life.

The misuse scenario described above in relation to dry powder inhaler 100 in accordance with the first embodiment of the invention applies also applies mutatis mutandis to the dry powder inhaler 200 in accordance with the second embodiment of the invention. Thus, the user may move the cover anticlockwise from the first (fully closed) position by only a part of the 120° towards the second (fully open) position to a part open position, and then can move the cover clockwise or anticlockwise to any position between the part open position and the first (fully closed) position without releasing a dose of medicament from a portion of the blister strip in the dispensing station contained within the housing 202 (i.e. without actuating the dry powder inhaler 200). However, any further anticlockwise movement of the cover forward from the part open position towards the second (fully open) re-engages the rotation control member 220 with the driving plate 210, such that a dose of medicament is released once the driving plate 210 has been rotated through a full 120° movement.

The invention claimed is:

1. A medicament dispenser for use with at least one medicament carrier carrying multiple distinct medicament dose portions, the medicament dispenser comprising: (a) a dispensing mechanism actuable for dispensing the dose portions carried by the at least one medicament carrier; (b) a mouthpiece; and (c) a cover for the mouthpiece, the cover being movably mounted to the dispenser for sequential movement from a closed position in which the mouthpiece is covered, to an open position in which the mouthpiece is partially uncovered, via a first position, and to a second position in which the mouthpiece is fully uncovered, such that the first position is between the second position and the closed position;

wherein the cover is adapted to couple with the dispensing mechanism such that:

movement of the cover from the closed position to the second position results in full actuation of the dispensing mechanism; and wherein the cover is adapted to couple with the dispensing mechanism such that:

movement of the cover from the closed position to the first open position results in partial actuation of the dispensing mechanism; return movement of the cover from the first position to the closed position does not result in actuation of the dispensing mechanism; and subsequent movement of the cover from the closed position to a distance equal to the distance between the closed and second positions less the distance between the closed and first positions results in full actuation of the dispensing mechanism, but any further movement of the cover to the second position does not result in actuation of the dispensing mechanism.

2. The medicament dispenser of claim 1, comprising:

a rotation control member;

a driving plate, to drive stepwise advancement of the dose portions to the dispensing mechanism, the driving plate comprising a camming feature and ratchet teeth; and a body comprising a slot;

wherein the rotation control member is driven between a rest state and an actuated state via an intermediate state by reciprocal movement of the cover between the closed position and the open position;

wherein the driving plate is mounted for reciprocal movement between a disengagement plane and an engagement plane, the camming feature and slot together allowing the driving plate to be moved reciprocally between the disengagement plane and the engagement plane;

wherein when the rotation control member moves from the rest state to the intermediate state, the rotation control member engages with the ratchet teeth to move the driving plate from its disengagement plane to its engagement plane;

wherein movement of the rotation control member in the intermediate state away from the actuated state is arranged to disengage the rotation control member from the driving plate; and wherein movement of the rotation control member in the intermediate state towards the actuated state is arranged to engage the rotation control member with the ratchet teeth to move the driving plate, such that the driving plate is rotatable in a drive direction to drive stepwise advancement of the dose portions.

3. The medicament dispenser of claim 2, wherein when the rotation control member moves from the rest state to the intermediate state, the rotation control member urges the camming feature against an inclined wall of the slot to move the driving plate from its disengagement plane to its engagement plane.

4. The medicament dispenser of claim 3, wherein when the rotation control member is in its rest state, the rotation control member is biased against the camming feature.

5. The medicament dispenser of claim 2, wherein the body comprises a second slot, and wherein when the rotation control member moves from the intermediate to the actuated state, the rotation control feature moves the camming feature into the second slot to move the driving plate from its engagement plane to its disengagement plane.

6. The medicament dispenser of claim 5, wherein the second slot has a wall directed transverse to the engagement plane such as to provide a cliff edge for the camming feature as it is urged round, whereby the camming feature passes into the second slot when the control member moves from the intermediate to the actuated state.

7. The medicament dispenser of claim 2, wherein the driving plate is biased towards the disengagement plane.

8. The medicament dispenser of claim 2, wherein the driving plate comprises an annulus connected to a central shaft by one or more flexible legs.

9. The medicament dispenser of claim 2, wherein rotation of the driving plate in a direction opposite to the drive direction is prevented by means of a ratchet.

10. The medicament dispenser of claim 2, wherein the rotation control member and the driving plate are mounted about a common axis.

11. The medicament dispenser of claim 2, wherein the rotation control member comprises at least one flexible arm extending in a circular arc, wherein the at least one flexible arm is arranged to engage the camming feature or ratchet teeth to move the driving plate.

12. The medicament dispenser of claim 11, wherein the rotation control member comprises three flexible arms.

13. The medicament dispenser of claim 12, wherein the camming feature extends radially outwardly from the annulus of the driving plate, optionally wherein the camming feature has an angled surface extending in a circumferential direction.

14. The medicament dispenser of claim 13, wherein the driving plate is rotatable in an anticlockwise direction, when viewed from the rotation control member, whereby the angled surface extends in the anticlockwise direction.

15. A medicament dispenser comprising:

a patient manual interface;

a rotation control member;

a driving plate, to drive stepwise advancement of dose portions to a dispensing station for inhalation by a patient, the driving plate comprising a camming feature and ratchet teeth; and a body comprising a slot;

wherein the rotation control member is driven between a rest state and an actuated state via an intermediate state by reciprocal movement of the patient manual interface between a rest state and an actuated state;

wherein the driving plate is mounted for reciprocal movement between a disengagement plane and an engagement plane, the camming feature and slot together allowing the driving plate to be moved reciprocally between the disengagement plane and the engagement plane;

wherein when the rotation control member moves from the rest state to the intermediate state, the rotation control member engages with the ratchet teeth to move the driving plate from its disengagement plane to its engagement plane;

wherein movement of the rotation control member in the intermediate state away from the actuated state is arranged to disengage the rotation control member from the driving plate; and wherein movement of the rotation control member in the intermediate state towards the actuated state is arranged to engage the rotation control member with the ratchet teeth to move the driving plate, such that the driving plate is rotatable in a drive direction to drive stepwise advancement of the dose portions.

* * * * *